(12) United States Patent
Fujimori (10) Patent No.: US 9,693,460 B2
(45) Date of Patent: Jun. 27, 2017

(54) WIRING BOARD, MANUFACTURING METHOD FOR WIRING BOARD, AND IMAGE PICKUP APPARATUS

(71) Applicant: OLYMPUS CORPORATION, Tokyo (JP)

(72) Inventor: Noriyuki Fujimori, Suwa (JP)

(73) Assignee: Olympus Corporation, Tokyo (JP)

( * ) Notice: Subject to any disclaimer, the term of this patent is extended or adjusted under 35 U.S.C. 154(b) by 253 days.

(21) Appl. No.: 14/017,849

(22) Filed: Sep. 4, 2013

(65) Prior Publication Data

US 2014/0003018 A1 Jan. 2, 2014

Related U.S. Application Data

(63) Continuation of application No. PCT/JP2011/078704, filed on Dec. 12, 2011.

(30) Foreign Application Priority Data

Mar. 4, 2011 (JP) ................................ 2011-048083

(51) Int. Cl.
*H05K 1/00* (2006.01)
*H05K 1/18* (2006.01)
(Continued)

(52) U.S. Cl.
CPC ............ *H05K 1/181* (2013.01); *A61B 1/0011* (2013.01); *A61B 1/051* (2013.01); *H04N 5/2251* (2013.01);
(Continued)

(58) Field of Classification Search
CPC ........ H01L 2924/01079; H05K 1/0213; H05K 1/0216; H05K 1/0218; H05K 1/0219;
(Continued)

(56) References Cited

U.S. PATENT DOCUMENTS 4,890,159 A * 12/1989 Ogiu .................. A61B 1/00045
348/231.99
4,918,521 A * 4/1990 Yabe .................. A61B 1/00179
348/373
(Continued)

FOREIGN PATENT DOCUMENTS

JP 64-19325 A 1/1989
JP 04-034873 A 2/1992
(Continued)

OTHER PUBLICATIONS

JP 06-85465 Abstract and Description English Translation.*
(Continued)

*Primary Examiner* — Pete Lee
(74) *Attorney, Agent, or Firm* — Scully, Scott, Murphy & Presser, P.C.

(57) ABSTRACT

A wiring board includes a plurality of wiring layers, a plurality of insulating layers, and an electrode member made of a conductive material, the electrode member being incorporated in the wiring board in a state in which the electrode member includes exposed sections on side surfaces that cross the plurality of wiring layers and the plurality of insulating layers.

2 Claims, 6 Drawing Sheets

(51) Int. Cl.
*A61B 1/05* (2006.01)
*H04N 5/225* (2006.01)
*H05K 3/40* (2006.01)
*H05K 3/10* (2006.01)
*A61B 1/00* (2006.01)
*H05K 3/00* (2006.01)
*H05K 3/46* (2006.01)

(52) U.S. Cl.
CPC ............... *H05K 1/18* (2013.01); *H05K 3/10* (2013.01); *H05K 3/403* (2013.01); *H05K 1/186* (2013.01); *H05K 3/0052* (2013.01); *H05K 3/4602* (2013.01); *H05K 2201/0919* (2013.01); *H05K 2201/10121* (2013.01); *H05K 2201/10356* (2013.01); *H05K 2201/10416* (2013.01); *H05K 2201/10446* (2013.01); *Y10T 29/49162* (2015.01)

(58) Field of Classification Search
CPC .. H05K 1/0224; H05K 1/0227; H05K 1/0228; H05K 1/0236; H05K 1/0237; H05K 1/0239; H05K 1/024; H05K 1/0242; H05K 1/0245; H05K 1/0246; H05K 1/0248; H05K 1/025; H05K 1/0253; H05K 2201/10356; H05K 2201/10416; H05K 2201/10446; H05K 1/181; H05K 1/18; H05K 1/186; H05K 3/0052; H05K 3/403; H05K 2201/0919; H05K 2201/10121; H05K 3/10; Y10T 29/49162; A61B 1/051; A61B 1/0011; H04N 5/2251
USPC .................................. 174/255–260
See application file for complete search history.

(56) References Cited

U.S. PATENT DOCUMENTS

| | | | | |
|---|---|---|---|---|
| 5,228,430 A | * | 7/1993 | Sakamoto | A61B 1/05 348/65 |
| 5,847,930 A | * | 12/1998 | Kazle | H01L 25/165 174/527 |
| 6,567,115 B1 | * | 5/2003 | Miyashita | A61B 1/051 348/76 |
| 6,627,997 B1 | * | 9/2003 | Eguchi | H01L 21/565 257/713 |
| 7,189,596 B1 | * | 3/2007 | Mu | H01L 23/49816 257/E23.069 |
| 2002/0117753 A1 | | 8/2002 | Lee et al. | |
| 2003/0096495 A1 | * | 5/2003 | Ihara | H01L 24/11 438/614 |
| 2004/0057220 A1 | | 3/2004 | Tamaki et al. | |
| 2004/0218084 A1 | | 11/2004 | Komoro et al. | |
| 2006/0231935 A1 | | 10/2006 | Nishida | |
| 2010/0006334 A1 | * | 1/2010 | Takenaka | H05K 3/465 174/262 |
| 2011/0034769 A1 | * | 2/2011 | Adair | A61B 1/00016 600/110 |

FOREIGN PATENT DOCUMENTS

| | | |
|---|---|---|
| JP | 06-085465 A | 3/1994 |
| JP | 07-221462 A | 8/1995 |
| JP | 11-284342 A | 10/1999 |
| JP | 2000-199863 A | 7/2000 |
| JP | 2002-076314 A | 3/2002 |
| JP | 2005-198964 A | 7/2005 |
| JP | 2006-294976 A | 10/2006 |
| JP | 2007-081071 A | 3/2007 |
| JP | 2008-251767 A | 10/2008 |

OTHER PUBLICATIONS

Hayashi (JP 06-085465 Description and Abstract English Translation).*

Extended Supplementary European Search Report dated Feb. 19, 2015 from related European Application No. 11 86 0278.8.

International Search Report dated Feb. 14, 2012 issued in PCT/JP2011/078704.

* cited by examiner

WIRING BOARD, MANUFACTURING METHOD FOR WIRING BOARD, AND IMAGE PICKUP APPARATUS

CROSS REFERENCE TO RELATED APPLICATION

This application is a continuation application of PCT/JP2011/078704 filed on Dec. 12, 2011 and claims benefit of Japanese Application No. 2011-048083 filed in Japan on Mar. 4, 2011, the entire contents of which are incorporated herein by this reference.

BACKGROUND OF THE INVENTION

1. Field of the Invention

The present invention relates to a wiring board disposed between a component such as an image pickup device chip and a wiring cable, a manufacturing method for the wiring board, and an image pickup apparatus including the wiring board.

2. Description of the Related Art

An image pickup apparatus including an image pickup device chip of a wafer level chip size package (WL-CSP) type is used for an application in which a reduction in size (a reduction in diameter) of an endoscope or the like is required. For example, Japanese Patent Application Laid-Open Publication No. 2005-198964 discloses an image pickup apparatus for an endoscope in which the image pickup device chip of the WL-CSP type is mounted on a wiring board.

SUMMARY OF THE INVENTION

A wiring board according to an embodiment of the present invention includes: a plurality of wiring layers; a plurality of insulating layers; and an electrode member made of a conductive material, the electrode member being incorporated in the wiring board in a state in which the electrode member includes an exposed section on a side surface that crosses the plurality of wiring layers and the plurality of insulating layers.

A manufacturing method for a wiring board according to another embodiment of the present invention includes: a substrate manufacturing step for manufacturing a wiring substrate including a plurality of wiring layers and a plurality of insulating layers and incorporating an electrode forming member made of a conductive material; and a cutting step for cutting the wiring substrate such that a part of the electrode forming member is exposed on a side surface.

An image pickup apparatus according to still another embodiment of the present invention includes: an image pickup device chip including an image pickup device on a first principal plane and including an electrode for external connection on a second principal plane; a wiring cable; and a wiring board including a plurality of wiring layers, a plurality of insulating layers, and a plurality of electrode members made of a conductive material, the plurality of electrode members being incorporated in the image pickup apparatus in a state in which the plurality of electrode members include exposed sections on side surfaces that cross the plurality of wiring layers and the plurality of insulating layers, the exposed section of one of the electrode members being joined to the electrode for external connection of the image pickup device chip, and the exposed section of another one of the electrode members being connected to the wiring cable.

DETAILED DESCRIPTION OF THE PREFERRED EMBODIMENT

<First Embodiment>

Figure 1:
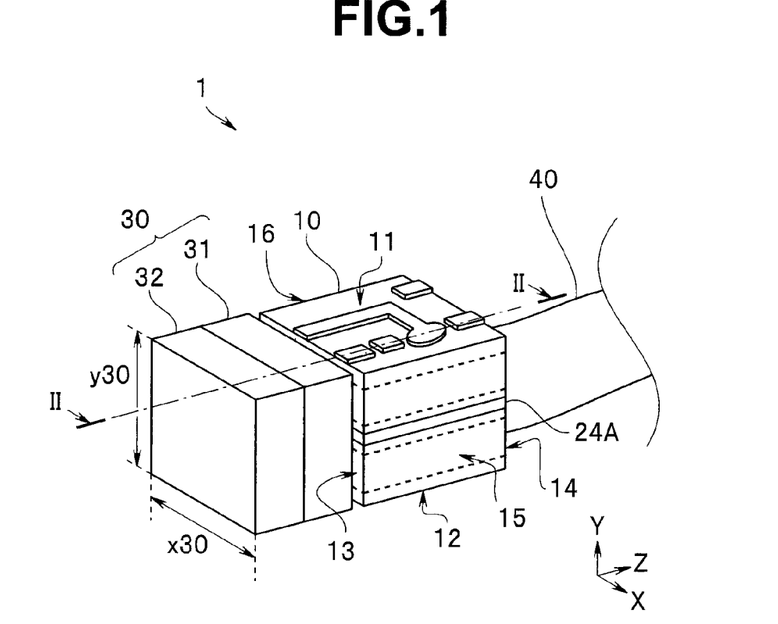
FIG. 1 is a perspective view of an image pickup apparatus in a first embodiment.

As shown in FIG. 1, an image pickup apparatus 1 in a first embodiment includes a wiring board 10, an image pickup section 30, and a wiring cable 40. The image pickup section 30 includes an image pickup device chip 31 and a transparent cover section 37. The wiring board 10 in the first embodiment is a substantially rectangular parallelepiped including a first principal plane 11, a second principal plane 12, and four side surfaces 13, 14, 15, and 16. Note that the first principal plane 11 and the second principal plane 12 are surfaces parallel to a core substrate 24A of the wiring board 10, which is a multilayer wiring board, and the side surfaces 13, 14, 15, and 16 are surfaces orthogonal to the core substrate 24A.

Maximum dimensions in XY directions of the image pickup apparatus 1 are dimensions x30×y30 of the image pickup section 30. Therefore, a reduction in size and, in particular, a reduction in diameter with small dimensions in the XY directions is realized.

Figure 2:
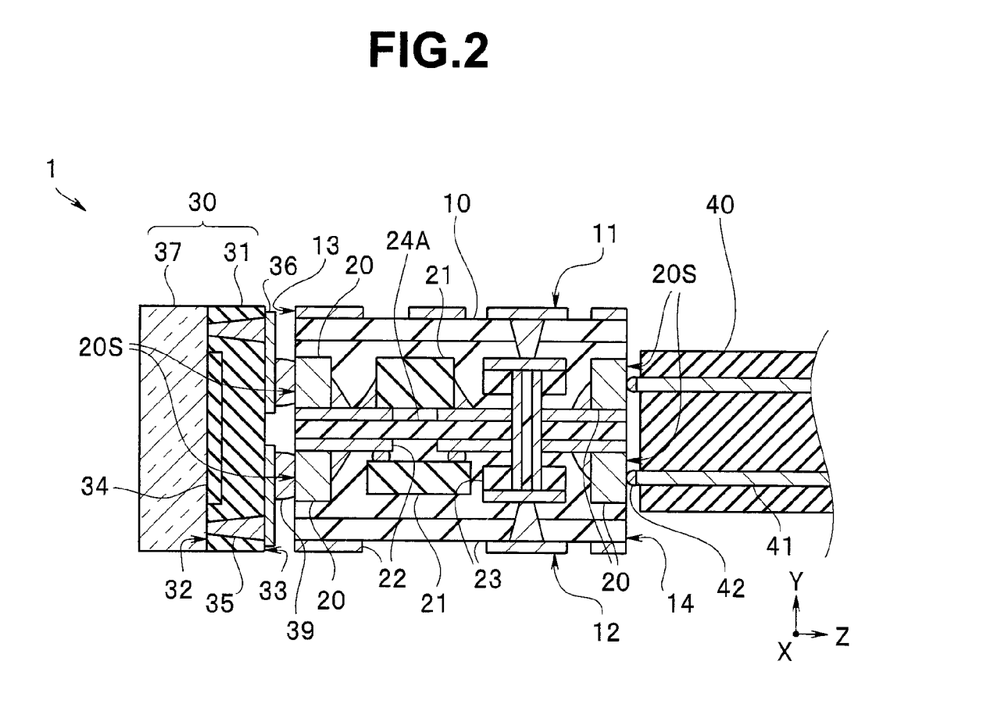
FIG. 2 is a sectional view of the image pickup apparatus in the first embodiment taken along line II-II in FIG. 1.

FIG. 2 is a cross section taken along line II-II in FIG. 1. As shown in FIG. 2, the image pickup device chip 31 is configured by a semiconductor in which an image pickup device 34 such as a CMOS image pickup device is formed on a first principal plane 32. The image pickup device 34 is connected to electrodes for external connection 39 of a second principal plane 33 via through-wires 35 and wires 36 of the second principal plane 33. That is, the image pickup device chip 31 is a chip for a so-called wafer level chip size package.

The wiring board 10 is a multilayer wiring board in which a plurality of wiring layers 22 and a plurality of insulating layers 23 are laminated on and under the core substrate 24A. As explained above, the first principal plane 11 and the second principal plane 12 are outer surfaces parallel to the wiring layers 22 and the insulating layers 23 and the side surfaces 13 to 16 are outer surfaces that cross the wiring layers 22 and the insulating layers 23 at a right angle. The wiring board 10 includes, on each of the side surfaces 13 and 14, four pattern sections (lands) made of a conductive material, i.e., exposed sections 20S, which are electrodes for external connection.

Figure 3:
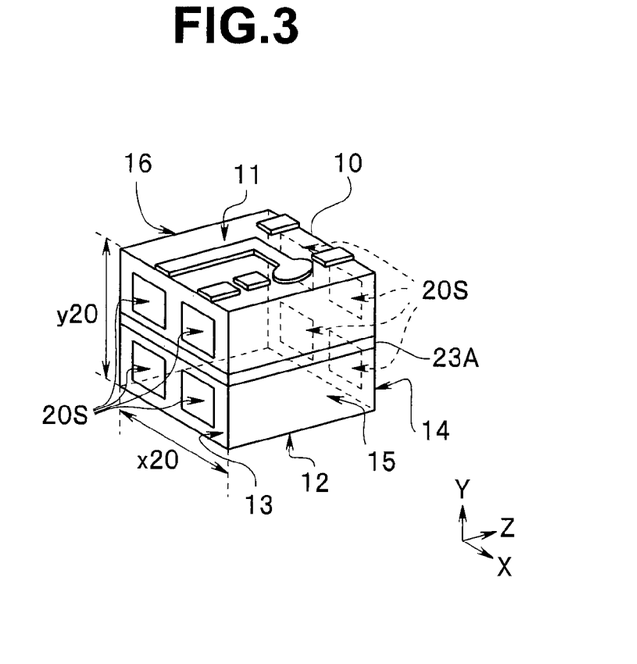
FIG. 3 is a perspective view of a wiring board in the first embodiment.
Figure 4:
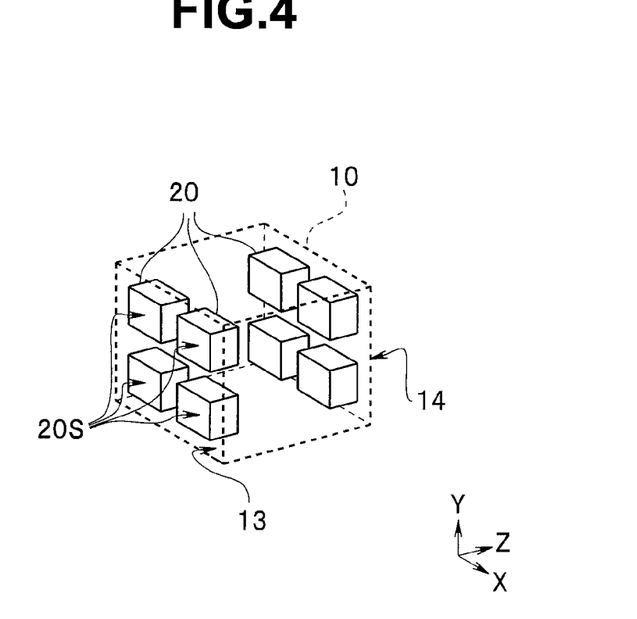
FIG. 4 is a perspective transparent view of the wiring board in the first embodiment.

As shown in FIGS. 3 and 4, the wiring board 10 incorporates eight electrode members 20 and includes, on each of the side surfaces 13 and 14, four exposed sections 20S. That is, the exposed sections 20S are not conductor patterns or the like formed on surfaces of the side surfaces 13 and 14 but are one surface of the bulk electrode member 20, which is a metallic ingot, incorporated in the wiring board 10. Note that, in the present embodiment, a shape of the exposed sections 20S is a substantially square shape. However, the shape of the exposed sections 20S may be a circular shape, a rectangular shape, or other shapes suitable for connection according to the sectional shape of the electrode members 20.

As shown in FIG. 1, the exposed sections 20S are electrodes not exposed on the first principal plane 11 and the second principal plane 12 and independent from electrodes formed on the first principal plane 11 and the second principal plane 12. The exposed sections 20S exposed only on the side surfaces are one surface of the electrode member 20 incorporated in the wiring board 10. Therefore, the exposed sections 20S do not peel off the side surfaces unlike electrode films formed on the side surfaces and reliability of joining is high. The electrode members 20 are manufactured from an electrode forming member 20A, which is a chip-shape metal, as explained below rather than forming a thick metal film. Therefore, the electrode members 20 are easily manufactured. A deficiency due to internal stress or the like does not occur.

It is preferable from the viewpoint of workability that the electrode members 20 are conductive material chip members and, in particular, made of a metal material such as copper or gold.

Note that dimensions x20×y20 (see FIG. 3) of the side surfaces 13 and 14 of the wiring board 10 are smaller than dimensions x30×y30 (see FIG. 1) of a principal plane of the image pickup section 30. That is, x20<x30 and y20<y30.

The wiring board 10 is a so-called component incorporating substrate in which not only the electrode member 20 but also an electronic component (a chip component) 21 such as a chip resistor or a chip capacitor is incorporated. In the wiring board 10, the electronic component 21 and the wiring layers 22 form a circuit configured to process input and output signals to and from the image pickup device chip 31.

A wiring board in which the electronic component 21 such as a passive component or an active component is incorporated has high functionality but is small in size.

Note that, as explained below, electronic components may be surface-mounted on the first principal plane 11 and the second principal plane 12 of the wiring board 10.

Next, a manufacturing method for the image pickup apparatus 1 and the wiring board 10 is explained. The wiring board 10 is manufactured by cutting a wiring substrate 10A. An electrode forming member 20A incorporated in the wiring substrate 10A is cut, whereby the electrode members 20 including the exposed sections 20S on the side surfaces are manufactured.

<Wiring Board Manufacturing Step>

FIGS. 5A to 5F are sectional views on a YZ plane for explaining the manufacturing method for the wiring board 10. A region including three wiring boards 10 is shown. First, the wiring substrate 10A in which the electrode forming member 20A made of a conductive material is incorporated is manufactured. Note that, in the following explanation, each of a plurality of wiring layers 22A to 22C of the wiring board 10 is referred to as wiring layers 22 and each of a plurality of insulating layers 23A to 23C is referred to as insulating layers 23.

The wiring substrate 10A is a substrate including components of a plurality of the wiring boards 10. The wiring substrate 10A includes the components of the plurality of wiring boards 10 not only in a Z direction but also in an X direction. The wiring substrate 10A includes, for example, components of four hundred wiring boards 10 in a matrix shape of 20×20. The four hundred wiring boards 10 are manufactured by cutting the wiring substrate 10A along the X direction and the Z direction.

Figure 5A:
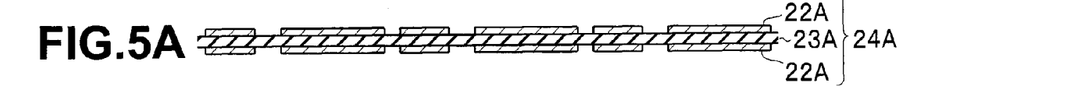
FIG. 5A is a sectional view for explaining a manufacturing method for the wiring board in the first embodiment.

As shown in FIG. 5A, in the manufacturing of the wiring substrate 10A, 20 μm-thick conductor films on both surfaces of a 150 μm-thick core (insulating layer) 23A of the core substrate 24A are patterned by etching, whereby the core substrate 24A including wiring layers 22A on both surfaces is manufactured.

Note that thickness of the core substrate 24A is set taking into account mounting height of incorporated components, thickness variation of the core substrate 24A, and the like.

Figure 5B:
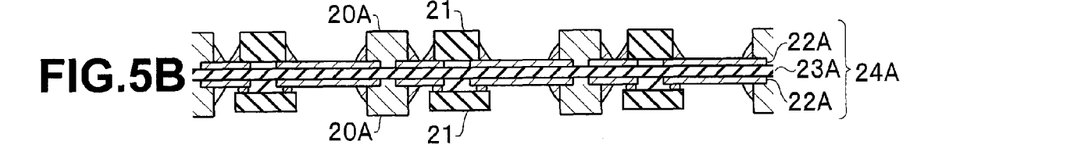
FIG. 5B is a sectional view for explaining the manufacturing method for the wiring board in the first embodiment.

Subsequently, as shown in FIG. 5B, the incorporated components, i.e., the electrode forming member 20A and the electronic component 21 are mounted on both side surfaces of the core substrate 24A.

A principal plane size (a mounting area) of the electrode forming member 20A is preferably a size same as or a size similar to a size of a general-purpose chip component such as a 0603 (6 mm×3 mm) size or a 0402 (4 mm×2 mm) size. This is because the electrode forming member 20A can be disposed in a predetermined position of a wiring board using a surface mount technology (SMT) same as a surface mount technology for the general-purpose chip component, for example, a component automatic insertion device.

Height of the electrode forming member 20A is determined according to specifications of the exposed sections 20S to be formed. Note that, when a plurality of the electrode forming members 20A are incorporated, the sizes of the electrode forming members 20A may be different.

For example, if the electrode forming members 20A having 0402 size height of 200 μm is mounted at an interval of 200 μm in the X direction, 200 μm-square electrodes (lands) are formed on a cut surface at a pitch of 400 μm. This is suitable for solder ball joining of a BGA (ball grid array).

The number of the electrode forming members 20A to be incorporated depends on the number of connection electrodes (the exposed sections 20S) formed on the side surface. For example, the number of the electrode forming members 20A is four to twelve.

In the mounting of the electrode forming members 20A, solder is printed on a connecting section of the wiring layers 22A and, after the electrode forming members 20A is provisionally joined on the solder, reflow treatment for the solder is performed. When the image pickup section 30 and the wiring cable 40 are joined to the manufactured wiring board 10 by solder, it is preferable to use high-melting point solder for the mounting of the electrode forming member 20A and the electronic component 21 incorporated in the wiring board 10.

Figure 5C:
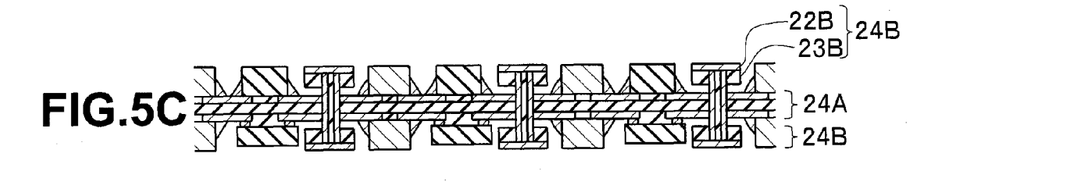
FIG. 5C is a sectional view for explaining the manufacturing method for the wiring board in the first embodiment.
Figure 5D:
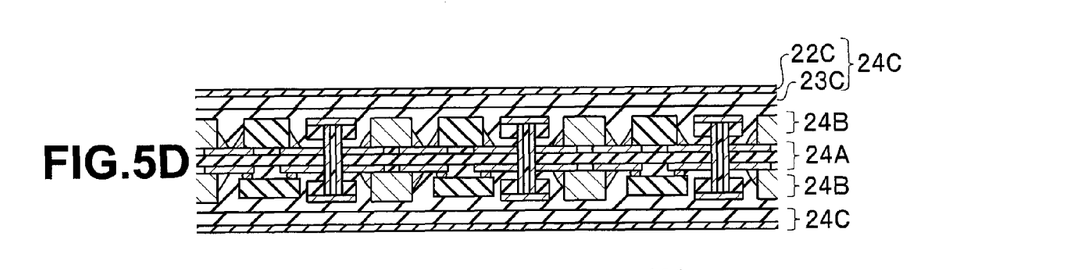
FIG. 5D is a sectional view for explaining the manufacturing method for the wiring board in the first embodiment.

Further, as shown in FIGS. 5C and 5D, a second laminated layer 24B including an insulating layer 23B and a wiring layer 22B is laminated using an adhesive for lamination. Regions of the second laminated layer 24B corresponding to already-mounted components are hollowed out. Therefore, the second laminated layer 24B does not interfere with the components during the lamination. Like the wiring layer 22A of the core substrate 24A, a desired circuit pattern is formed on the wiring layer 22B.

Note that electrical joining of the wiring layer 22B and the wiring layer 22A of the core substrate 24A may be performed by forming a micro-via or the like. Alternatively, electrical joining of three or more wiring layers may be collectively performed by forming a through-hole in a later process.

Further, a second laminated layer 24C including an insulating layer 23C and a wiring layer 22C is laminated using the adhesive for lamination. Unlike the first laminated layer 24B, the second laminated layer 24C is a planar plate without a hollow-out like a laminated layer of a normal build-up substrate. Like the wiring layer 22B, the wiring layer 22C may be electrically joined to other wiring layers via a micro-via or the like. Alternatively, the wiring layer 22C and the other wiring layers may be collectively electrically joined via a through-hole in a later process. At this point, the adhesive for lamination is applied sufficiently thick to, in particular, peripheral sections of the incorporated components to prevent gaps from being formed around the incorporated components. Further, a through-hole is formed to collectively electrically join the respective layers. That is, publicly-known multilayer wiring board manufacturing methods are used in combination in the manufacturing of the wiring substrate 10A. For example, the number of laminations of the wiring layers 22 and the insulating layers 23 of the wiring substrate 10A, i.e., the wiring board 10 is determined according to specifications.

The wiring layer 22C of the second laminated layer 24C is etched to form a wiring pattern, whereby the wiring substrate 10A is manufactured.

<Cutting Step>

Figure 5E:
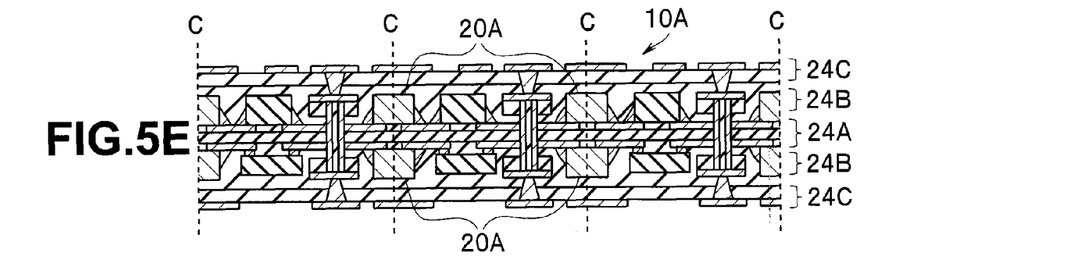
FIG. 5E is a sectional view for explaining the manufacturing method for the wiring board in the first embodiment.

As shown in FIG. 5E, the wiring substrate 10A is singulated into a plurality of the wiring boards 10 by cutting. At this point, the wiring substrate 10A is cut along a cutting line C such that a part of the electrode forming member 20A is exposed on a cut surface (a side surface). When the wiring substrate 10A is cut along the cutting line C, which is an incorporating position of the electrode forming member 20A, the electrode forming member 20A is changed to the electrode members 20 of respective two wiring boards 10. In other words, one electrode forming member 20A is changed to two electrode members 20 by the cutting.

Figure 5F:
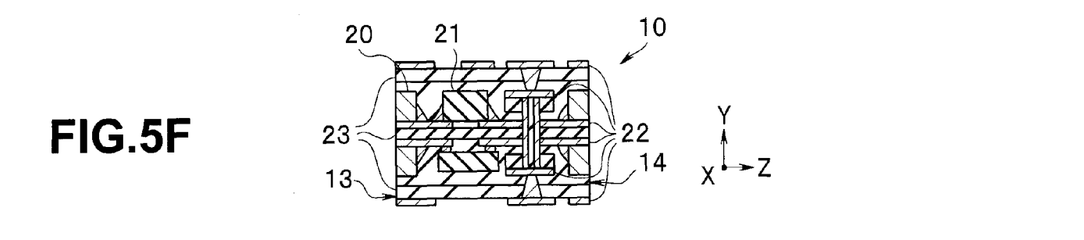
FIG. 5F is a sectional view for explaining the manufacturing method for the wiring board in the first embodiment.

That is, as shown in FIG. 5F, the electrode forming member 20A is changed to the electrode members 20 including the exposed sections 20S on the side surfaces by the cutting. In other words, the electrode members 20 are exposed on the side surfaces formed by the cutting.

In order to accurately specify a position of the electrode forming member 20A incorporated in the wiring substrate 10A, an internal structure detecting device or the like by an infrared ray or ultrasound may be used or a position specifying pattern may be formed on the outer surface (the first principal plane) when the wiring substrate 10A is manufactured. A dicing device used for cutting of a semiconductor wafer, a high-power laser beam machine, or the like is used for the cutting.

<Joining Step>

The wires 36 of the image pickup section 30 are connected to the electrode members 20, which are exposed on the side surface 13 of the wiring board 10, via the electrodes for external connection 39. Lead wires 41 of the wiring cable 40 are connected to the electrode members 20, which are exposed on the side surface 14 of the wiring board 10, via connecting sections 42.

The lead wires 41 of the wiring cable 40 are electric wires for transmitting input and output signals to and from the image pickup device 34 and are flexible cables for connecting the image pickup apparatus 1 and an image pickup device control section (not shown in the figure).

When the connection of the image pickup section 30 and the wiring cable 40 is performed by solder joining, internal connection solder of the wiring board 10 is sometimes melted again. However, since resin is filled around the wiring board 10, a position of the wiring board 10 does not move and a connection state is maintained. By using the high-melting point solder for the internal connection of the wiring board 10 as explained above, the internal connection state of the wiring board 10 is more stably maintained even during the connection of the image pickup section 30 and the wiring cable 40.

As explained above, the wiring board 10 is small in size because the wiring board 10 includes the plurality of wiring layers, the plurality of insulating layers, and the electrode member made of the conductive material, the electrode member being incorporated in the wiring board 10 in a state in which the electrode member includes the exposed section on the side surface that crosses the wiring layers and the insulating layers. The image pickup apparatus 1 including the wiring board 10 is small in size.

<Second Embodiment>

Next, an image pickup apparatus 1A in a second embodiment is explained. Since the image pickup apparatus 1A is similar to the image pickup apparatus 1, the same components are denoted by the same reference numerals and signs and explanation of the components is omitted.

Figure 6:
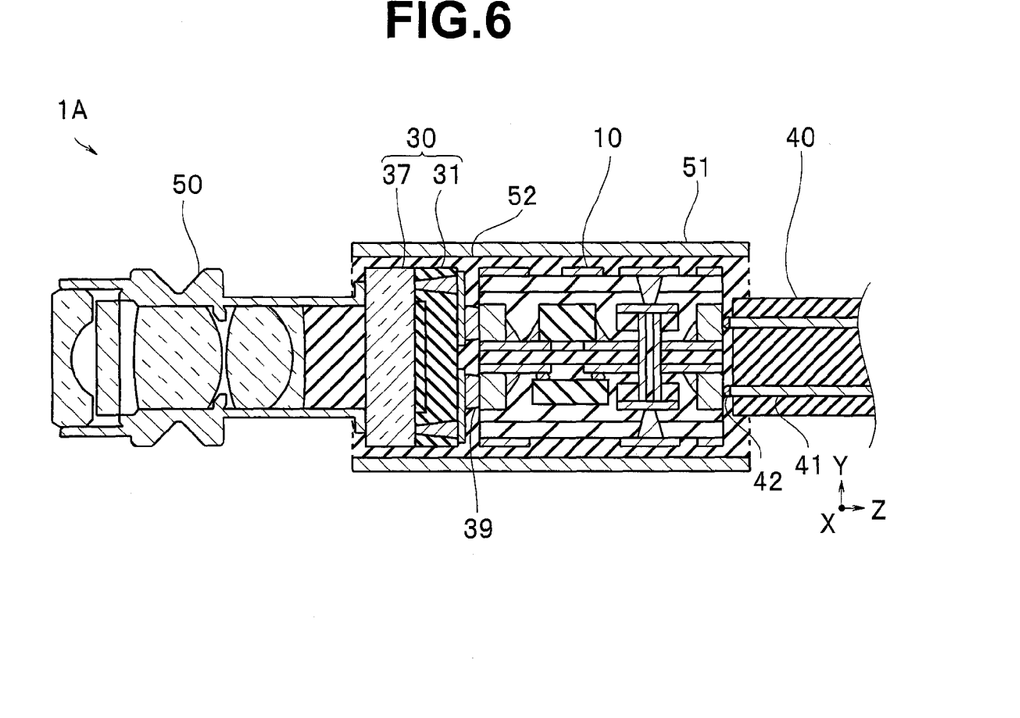
FIG. 6 is a sectional view of an image pickup apparatus according to a second embodiment.

As shown in FIG. 6, the image pickup apparatus 1A includes an optical system member 50 and a joining protection member 51 in addition to the components of the image pickup apparatus 1. The optical system member 50 disposed over the entire surface of the cover section 37 of the image pickup section 30 includes a plurality of lenses.

In the image pickup apparatus 1, the image pickup device chip 31 and the wiring board 10 are solder-joined by the electrodes for external connection 39 and further reinforced by a not-shown optical adhesive, semiconductor sealing agent, or the like. However, in some case, a joining area is small in size and bending strength is insufficient. In the image pickup apparatus 1A, joining strength of the image pickup device chip 31 and the wiring board 10 is reinforced by the joining protection member 51.

Therefore, the image pickup apparatus 1A has the effects of the image pickup apparatus 1 and further improves the bending strength.

Note that, in the image pickup apparatus 1A shown in FIG. 6, an example is shown in which a joining section of the wiring board 10 and the wiring cable 40 is also reinforced by the joining protection member 51.

Since the image pickup apparatus 1A is small in size and, in particular, small in diameter, the image pickup apparatus 1A can be preferably used as an image pickup apparatus of an endoscope.

<Third to Sixth Embodiments>

Next, wiring boards 10B to 10E in third to sixth embodiments are explained. Since the wiring boards 10B to 10E are similar to the wiring board 10, the same components are denoted by the same reference numerals and signs and explanation of the components is omitted.

Figure 7:
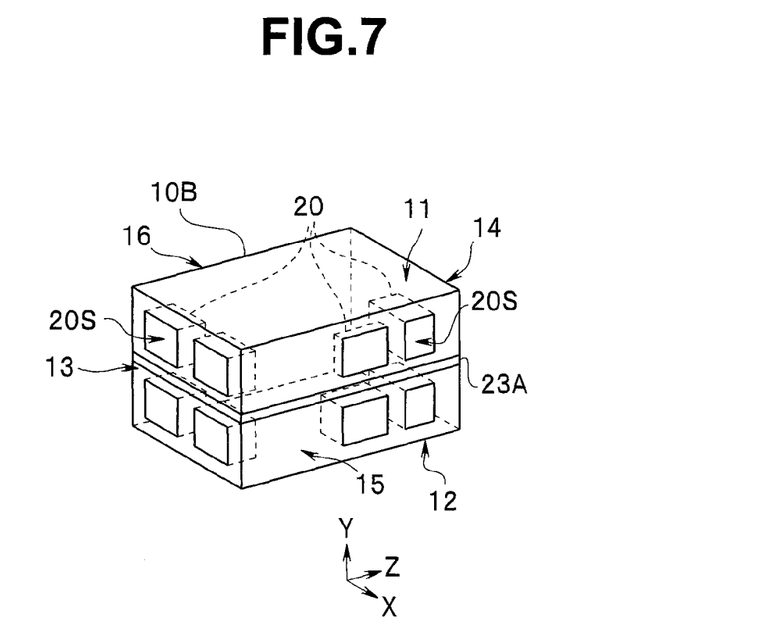
FIG. 7 is a perspective transparent view of a wiring board in a third embodiment.

As shown in FIG. 7, the wiring board 10B in the third embodiment incorporates the electrode members 20 including the exposed sections 20S on the side surface 13 and the side surface 15 orthogonal to the side surface 13. The wiring board 10B has the effects of the wiring board 10.

That is, the side surfaces on which the exposed sections 20S of the electrode members 20 of the wiring board are exposed are not limited to the opposed two side surfaces. Further, the exposed sections 20S may be exposed on three or more side surfaces. The exposed sections 20S functioning as electrodes (lands) for electrical connection to the outside may be present on all the side surfaces 13, 14, 15, and 16. Further, an electrode (a land) made of a conductor film for electrical connection to the outside may be formed on at least one of the first principal plane 11 and the second principal plane. Note that electric components such as chip components for forming an internal circuit may be mounted on the exposed sections 20S.

Figure 8:
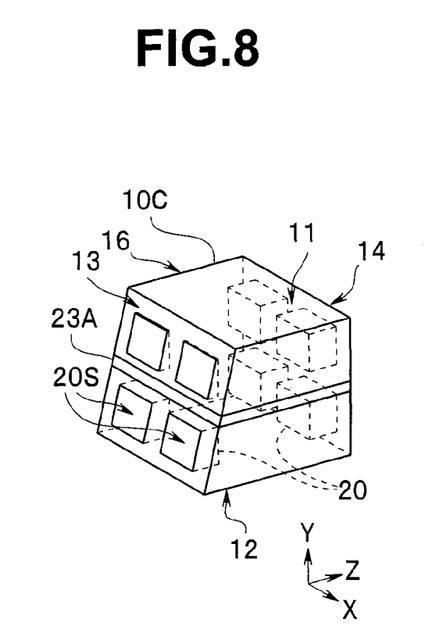
FIG. 8 is a perspective transparent view of a wiring board in a fourth embodiment.

On the other hand, in a wiring board 10C in the fourth embodiment shown in FIG. 8, the side surface 13 inclines without crossing the first principal plane 11 and the second principal plane 12 at a right angle. That is, cut surfaces (XY planes), which are exposed sections, of the electrode members 20 may incline and cross the core substrate 24A, i.e., the wiring layers 22 and the insulating layers 23 or may be curved surfaces rather than planes.

Further, an upper surface of the wiring board 10C, i.e., a side surface of the wiring board 10C when observed from a Y-axis direction may be a curve by milling or the like rather than a straight line by the dicing or the like.

Figure 9A:
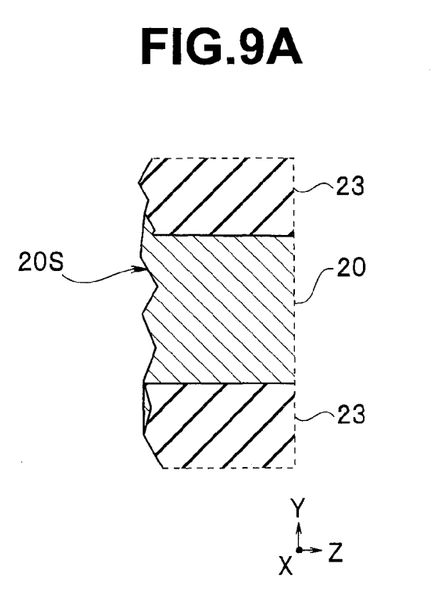
FIG. 9A is a sectional view for explaining an exposed section of a wiring board in a fifth embodiment.
Figure 9B:
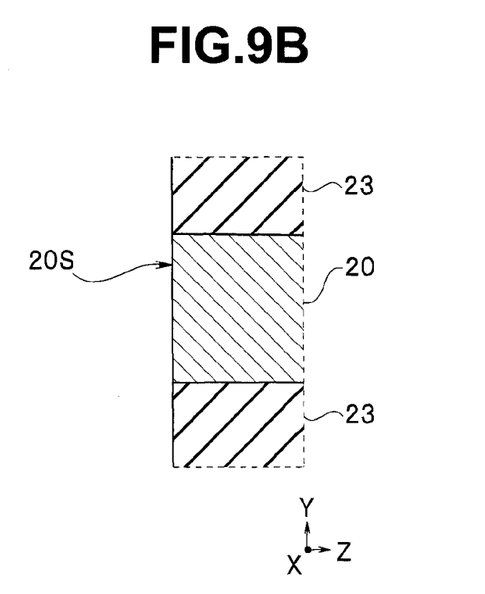
FIG. 9B is a sectional view for explaining the exposed section of the wiring board in the fifth embodiment.

In the wiring board 10D in a fifth embodiment shown in FIG. 9B, the exposed section 20S of the cut electrode member 20 is further polished. In the wiring board 10E in a sixth embodiment shown in FIG. 10, a conductive plating film 25 is further formed on the exposed section 20S of the polished electrode member 20.

As shown in FIG. 9A, depending on a machining method, surface roughness of a cut surface is sometimes large or the exposed section 20S is small or deformed because of deformation of the insulating layers 23 and the wiring layers 22. On the other hand, as shown in FIG. 9B, in the wiring board 10D, since the exposed section 20S is polished, reliability of joining is high.

Figure 10:
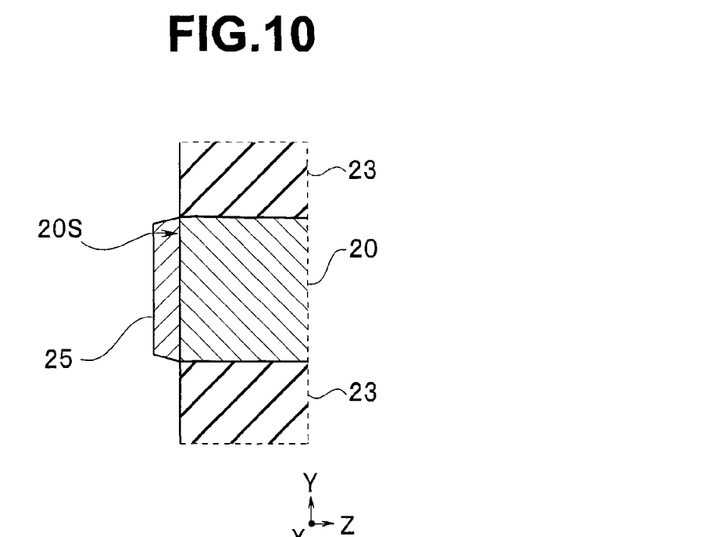
FIG. 10 is a sectional view for explaining an exposed section of a wiring board in a sixth embodiment.

In the wiring board 10E, on a surface of which the conductive plating film 25 of, for example, copper, nickel, tin, solder, or gold is formed, reliability of joining is higher.

<Seventh Embodiment>

Figure 11:
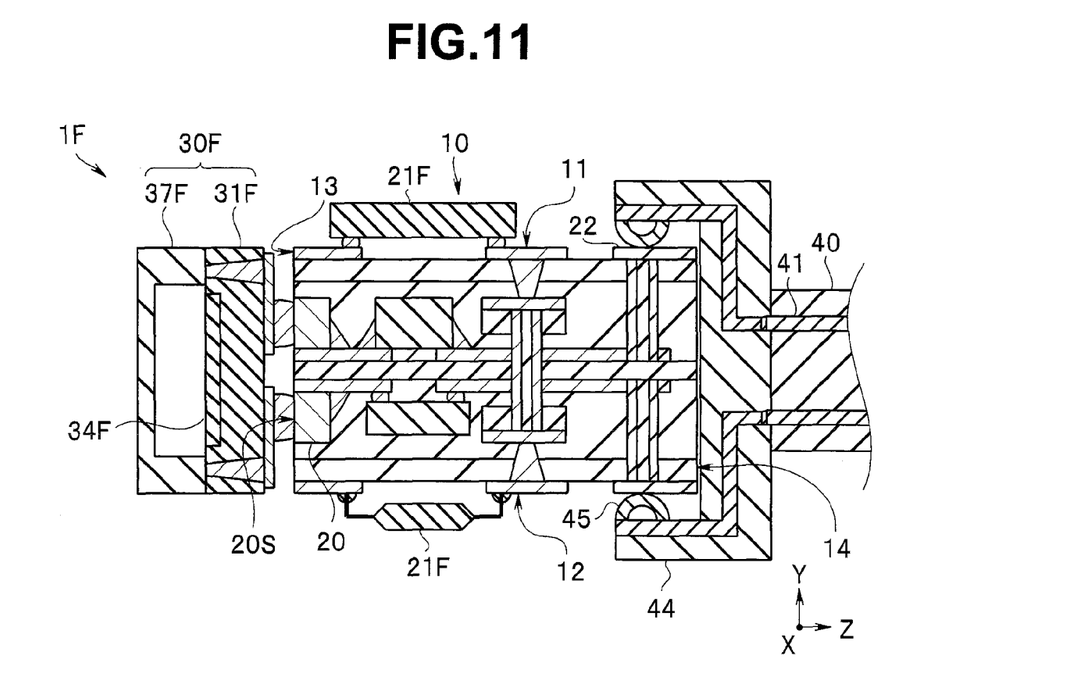
FIG. 11 is a sectional view of a sensor device including a wiring board in a seventh embodiment.

A wiring board 10F in a seventh embodiment shown in FIG. 11 configures a pressure sensor device 1F, which is a semiconductor device, in conjunction with a pressure sensor 30F and a socket 44 for wiring connection. That is, the pressure sensor 30F is mounted on the side surface 13 of the wiring board 10F and the socket 44 is inserted into the side surface 14.

A pressure sensor chip 31F configures the pressure sensor 30F in conjunction with a cover section 37F configured to protect an element section 34F. Although not shown in the figure, for example, the element section 34F is configured by a membrane, a piezoelectric film configured to detect deformation of the membrane, and the like.

A plurality of electrode sections 45 of the socket 44 are electrically connected to the respective wiring layers 22 of the first principal plane 11 and the second principal plane 12 of the wiring board 10F by being detachably fit with the wiring layers 22. The electrode sections 45 are connected to the lead wires 41 of the wiring cable 40.

That is, the wiring board 10F includes the exposed sections 20S of the electrode members 20 only on one side surface 13.

Note that electronic components 21F are surface-mounted on the wiring layers 22 of the first principal plane 11 and the second principal plane 12 of the wiring board 10F.

The wiring board 10F has the effects of the wiring board 10 and the like. Further, since the pressure sensor 30F is disposed at an end of the wiring board 10F, the pressure sensor 30F is less easily affected by other electronic components mounted on the wiring board 10F. Therefore, measurement accuracy of the sensor is high. A larger number of components can be mounted on the wiring board 10F without increasing the wiring board 10F in size.

The present invention is not limited to the embodiments explained above and various alterations, modifications, and the like of the embodiments can be made without departing from the spirit of the invention.

What is claimed is:

1. An image pickup apparatus comprising: a wiring board comprising: a core substrate having wiring layers on each of an upper surface and a lower surface of a core, the core being a first insulation layer, first plurality of electrode members and second plurality of electrode members, wherein each of the first plurality of electrode members and the second plurality of electrode members being made of a metal material, wherein each of the first plurality of electrode members and the second plurality of electrode members being arranged in a plurality of rows and columns on the core substrate and each of the first plurality of electrode members and the second plurality of electrode members being connected with the wiring layers; and a second insulating layer made of resin, the second insulating layer having a first part being disposed on the upper surface of the core and a second part disposed on the lower surface of the core and wherein the second insulating layer covers the first plurality of electrode members and the second plurality of electrode members; wherein end surfaces of the core substrate and end surfaces of the second insulating layer being exposed on each of a first side surface and a second side surface of the wiring board; end surfaces of the first plurality of electrode members and end surfaces of the second plurality of electrode members being exposed on the first side surface and the second side surface respectively, wherein the first plurality of electrode members and the second plurality of electrode members are formed from metallic ingots embedded into the first and second side surfaces of the wiring board such that a body of each of the metallic ingots is entirely positioned within an interior of the second insulating layer and a surface of the body of each of the metallic ingots is exposed on the first and second side surfaces of the wiring board; and an image pickup device chip comprising: an image pickup device disposed on a first principal plane of the image pickup device chip; and a plurality of wires for external connection on a second principal plane of the image pickup device chip, the plurality of wires for external connection being connected with the first plurality of electrode members exposed on the first side surface of the wiring board and a wiring cable connected with the second plurality of electrode members that are exposed on the second side surface of the wiring board.

2. The image pickup apparatus according to claim 1, further comprising a joining protection member disposed over outer surfaces of at least the image pickup device chip and the wiring board, the joining protection member being configured to reinforce a joining strength between at least the image pickup device chip and the wiring board.

* * * * *